US00PP08836P

United States Patent [19]

Lamb

[11] Patent Number: Plant 8,836

[45] Date of Patent: Jul. 12, 1994

[54] CALATHEA PLANT NAMED ROSY

[75] Inventor: Ann E. Lamb, Lake Placid, Fla.

[73] Assignee: Twyford International, Inc., Sebring, Fla.

[21] Appl. No.: 110,720

[22] Filed: Aug. 23, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

A Calathea plant named Rosy having rounded leaves variably marked in the center with pink and silvery green, bordered by a vary dark green margin.

3 Drawing Sheets

1

The present invention comprises a new and distinct cultivar of Calathea, botanically known as *Calathea roseo picta,* and referred to by the cultivar name Rosy.

The new cultivar is a random mutation and was discovered and selected from a group of *C. roseo picta* in Sebring, Fla. in July 1990 by the inventor Ann E. Lamb. Propagation by tissue culture increased the number of plants for evaluation and has demonstrated the stability of the combination of characteristics of Rosy from generation to generation.

The following observations, measurements and values were taken in Sebring, Fla. and describe plants grown in Apopka, Fla. under greenhouse conditions which closely approximate those generally used in horticultural practice.

The following traits have been repeatedly observed to be characteristics which in combination distinguish Rosy from others of the same species *C. roseo picta.*

1. The plant produces leaves having centers variably marked with metallic pink and silver-green. 2. The amount of pink in the center of the leaf varies with the age and maturity of the plant, from entirely pink when juvenile to becoming silvery-green with flecks of pink when mature.

All color references are to the Royal Horticultural Society Colour Chart. Colors may vary somewhat depending on horticultural practices such as light level and fertilization rate, among others, without, however, any variance in genotype.

In the accompanying color photographic drawings, the photograph on sheet 1 is a top perspective view of a plant of Rosy in a 10.2 cm pot approximately 13 weeks after planting a 16-week-old liner obtained by tissue culture and grown under appropriate growing conditions. The photographs on sheets 2 and 3 show plants of Rosy grown in 15.4 cm and 20.5 pots for 25 and 31 weeks, respectively. The photographs on sheets 1–3 illustrate the change in leaf color as the plant ages. Colors are as accurate as possible with color illustrations of this type.

Origin: Mutation of *Calathea roseo picta.*

Classification: *Calathea roseo picta,* cv, Rosy.

Propagation: Asexual production either by tissue culture or division.

Plant: In a 20.5 cm pot for a plant grown from a 16-week-old liner after 25 weeks under appropriate growing conditions, Rosy reaches a mature size of approximately 12 cm to 15 cm in height and 18 cm to 24 cm in width.

2

Leaves:

*Form.*—The leaf blade is orbicular with a mucronate tip and an obtuse base. The margins are entire. The midrib tends to curve slidghtly downward over the length of the leaf. The leaf blade is wavy over the width of the leaf.

*Size.*—Leaf blades of a mature-sized plant are approximately 12.5 cm to 13 cm in length and approximately 10.3 cm to 11.2 cm in width.

*Petiole.*—The petiole is approximately 8 cm to 9.5 cm in height from the base of the petiole to the base of the leaf blade on the primary shoot. Secondary shoots are somewhat smaller depending on the age of the shoot. The petiole is approximately 4 mm in diameter just below the geniculum, and the petiole below the geniculum is straight.

*Petiole wings.*—Petiole wings are approximately 6.5 cm in length and 7 mm in width at their midpoint. The tips of the petiole wings are rounded. There is approximately 1.2 cm to 1.5 cm between the top of the wing and the base of the geniculum.

*Geniculum.*—The geniculum is approximately 13 mm in length and 3 mm in diameter. The color is closest to 177 A but somewhat greener. There is no space between the top of the geniculum and the base of the leaf blade. The geniculum is prominent. The orientation of the leaf to the petiole is variable, as the geniculum bends. During the night and early morning, the geniculum is straight, and the leaf is held nearly straight above the petiole. During the day, the geniculum is bent, and the leaf is oriented approximately 90 degrees to the petiole.

*Veins.*—Veins and midrib are sunken, with the leaf blade slightly concave between veins on the upper surface. The midrib protrudes from the lower surface. Primary veins on leaves radiate out from the midrib along the length of the leaf. Veins are recessed within the leaf. There are approximately 12–14 primary viens on the leaf.

*Color.*—Upper surface: Margin: Darker than 139 A at all growth stages. Leaf center: 58 A with flecks of metallic 191 when juvenile, changing on subsequent growth as the plant matures to metallic 191 C with splashes of 58 A. Lower surface: Mature leaf, 187 A. Midrib: Upper surface 59 B-C, lower surface greener than 177A Petiole: Greener than 177 A Petiole wing: Lighter than 183 C-D.

Inflorescence: The inflorescence of Rosy is typical of the species *Calathea roseo picta* and has no commercial significance.

Roots: Dark brown fibrous roots with fine laterials.

GENERAL OBSERVATIONS

Calathea Rosy has rounded leaves with a pink and metallic silvery green center, bordered by a vary dark green margin. The amount of pink varies with the age of the plant, from nearly solid pink with flecks of silvery green when juvenile, to silivery green with flecks of pink when mature. These combined characteristics make Caltathea Rosy a unique new cultivar.

What is claimed is:

1. A new and distinct cultivar of Calathea plant named Rosy, as illustrated and described.

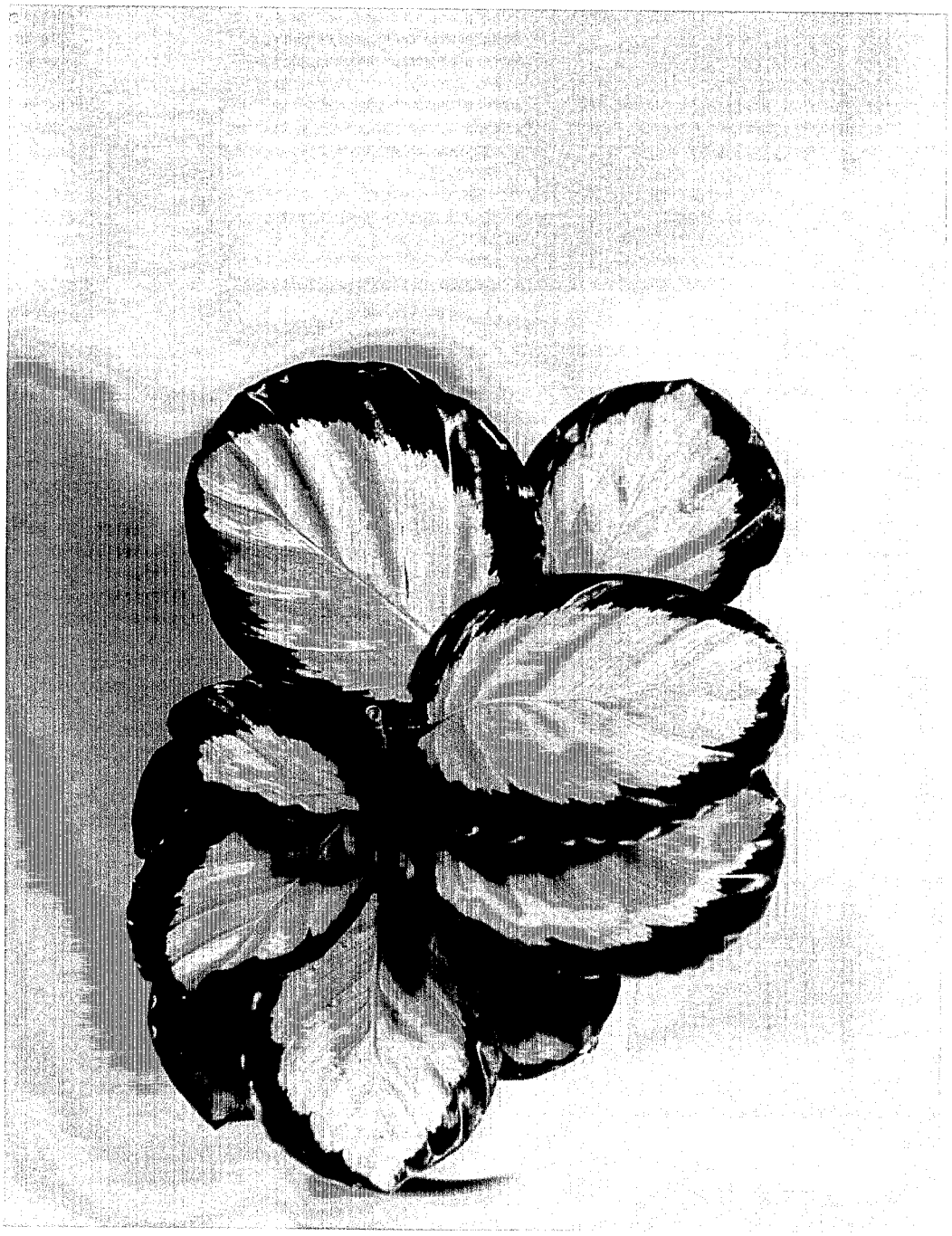

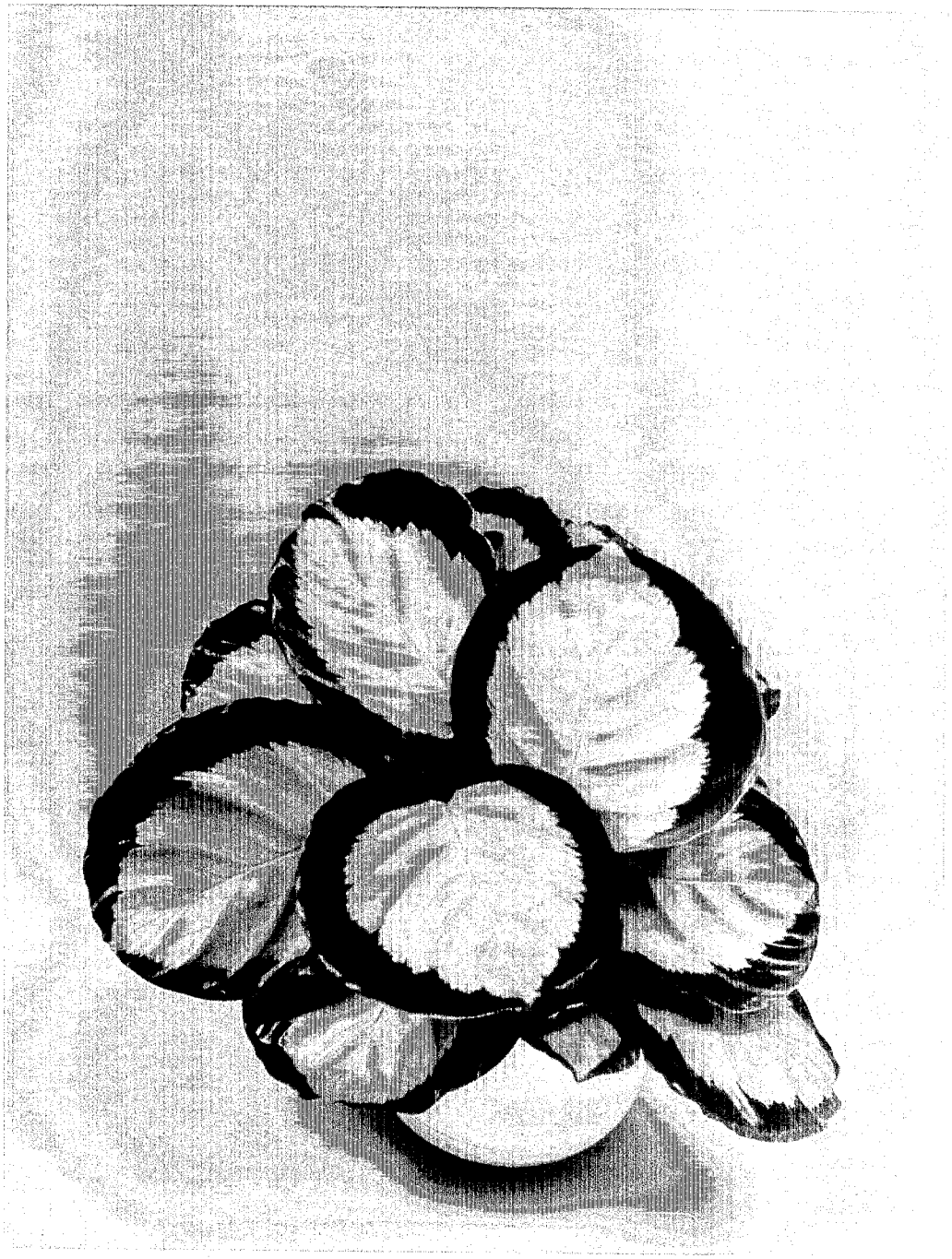

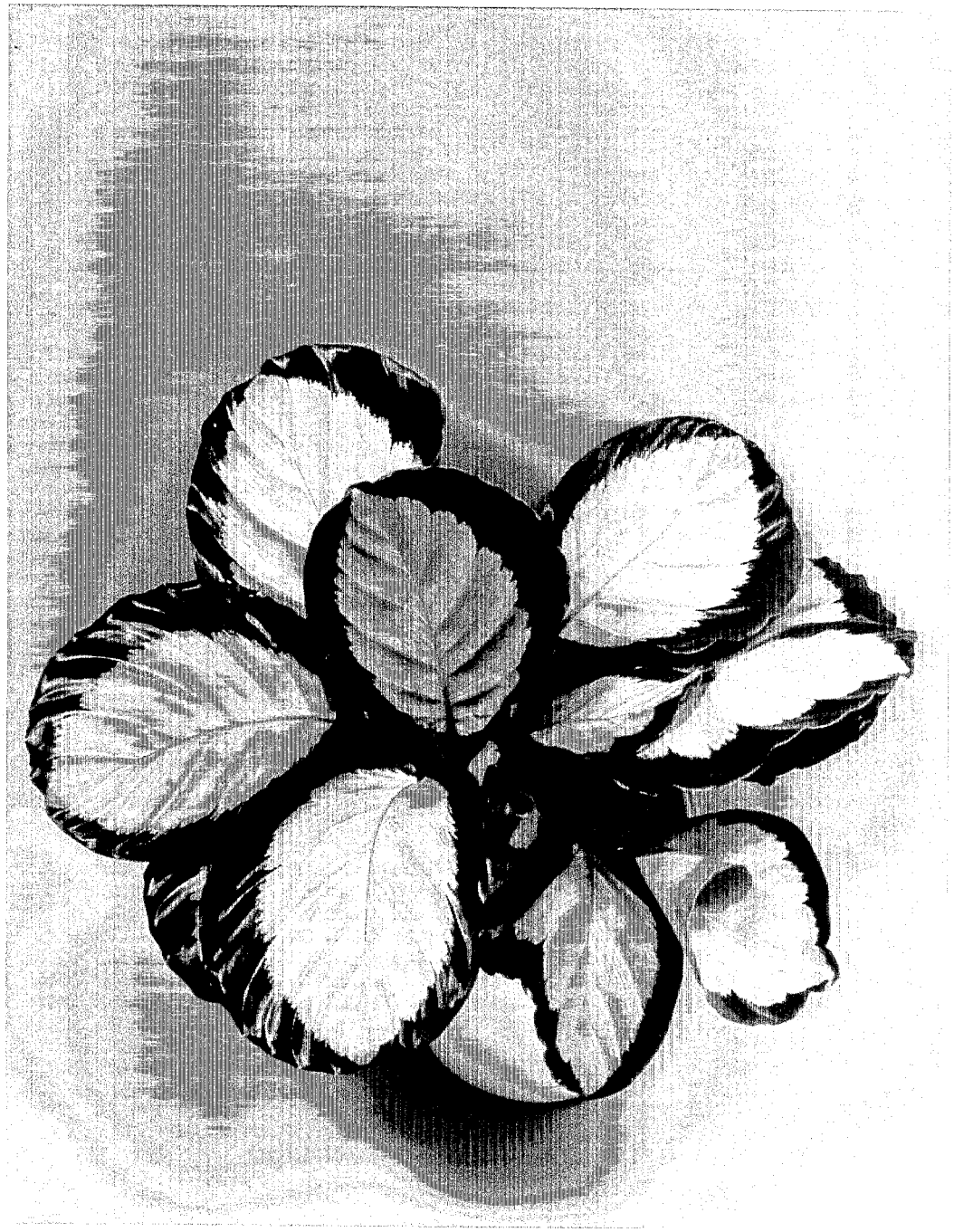

* * * * *